US00PP15220P3

(12) United States Plant Patent
Houbraken

(10) Patent No.: US PP15,220 P2
(45) Date of Patent: Oct. 12, 2004

(54) ***BIDENS FERULIFOLIA* PLANT NAMED 'BIDANTIS'**

(50) Latin Name: *Bidens ferulifolia*
Varietal Denomination: Bidantis

(75) Inventor: Anna M. W. P. Houbraken, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 66 days.

(21) Appl. No.: 10/339,804

(22) Filed: Jan. 10, 2003

(65) Prior Publication Data

US 2004/0139510 P1 Jul. 15, 2004

(51) Int. Cl.[7] ..... A01H 5/00

(52) U.S. Cl. ..... Plt./263

(58) Field of Search ..... Plt./263

*Primary Examiner*—Kent Bell

(74) *Attorney, Agent, or Firm*—Bruce Vrana; Edouard G. Lebel

(57) ABSTRACT

A distinct cultivar of *Bidens* plant named 'Bidantis' which is particularly distinguished by its vigorous character, upright (bit trailing) plant habit, dark green foliage and golden yellow inflorescences. The new cultivar can perfectly be used in mixed hanging baskets.

1 Drawing Sheet

Latin name of the genus and species of the plant claimed: *Bidens ferulifolia.*

Varietal denomination: 'Bidantis'.

BACKGROUND OF THE NEW PLANT

The present invention relates to a new distinct cultivar of *Bidens,* botanically known as *Bidens ferulifolia,* native to South USA and Mexico. The new cultivar is propagated by cuttings resulting from a seedling from *Bidens ferulifolia* cv. 'BQ001' (not patented). This new plant is an annual. The new cultivar is a product of a planned breeding program conducted by the inventor in Enkhuizen, The Netherlands. The objective of the breeding program was to develop an intermediate between the compact *Bidens* varieties and the very vigorous trailing *Bidens* varieties. As a result of an open pollination of *Bidens ferulifolium* BQ001 (unpatented and commercialised in Europe) the present cultivar was created in 1999 in Enkhuizen. 'Bidantis' was asexually reproduced by cuttings for 3 years now and trialled under different conditions in Europe on trial. The instant plant reproduces true to type in successive generations of asexual reproduction.

DESCRIPTION OF THE DRAWING

This new *Bidens* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Bidens* plant. The data which defines these characteristics were collected from asexual reproductions carried out in Enkhuizen, Netherlands. The plant history was taken on 13 weeks old plants, grown in hanging baskets in Enkhuizen, The Netherlands with day temperatures ranging from 16 and 20 degrees C., and night temperatures ranging from 12 to 14 degrees C. Color references are primarily to The R.H.S. Colour Chart of The Royal Horticultural Society of London.

TABLE 1

Differences between the new cultivar 'Bidantis' and two similar cultivars

| | 'Bidantis' | 'Bidtis-1' (U.S. Plant Pat. No. 12,280) | 'Peter's Goldteppich' (U.S. Plant Pat. No. 12,880) |
|---|---|---|---|
| Plant Height | 30–35 cm | 20 cm | 12 cm |
| Plant Width | 70–80 cm | 90 cm | 100 cm |
| Flower Color | More Golden than 9A | 12A | 12A |
| Flower Size | 3–3.5 cm | 3.4 cm | 4–5 cm |

The plant:

*Classification — Botanical.*—*Bidens ferulifolia* cv. 'Bidantis'.

Parentage:

*Female parent.*—Seedling selection of *Bidens ferulifolia* cv. 'BQ001', which has a trailing growth habit and a flower color yellow RHS 12A; Breeders code of the new plant is B 74-3.

*Male parent.*—Unidentified selection of *Bidens ferulifolia.*

Propagation:

*Type cuttings.*—Terminal cuttings.

*Time to initiated roots.*—10–12 days at air temperature of 21 degrees C.

*Time to develop roots.*—14–18 days at air temperature of 17 degrees C.

Plant description:

*Growth habit.*—Upright and little trailing.

*Plant height.*—30–35 cm.

*Vigor.*—Much more vigorous than 'Bidtis 1' and 'Peter's Goldteppich'.

*Spreading area of plant.*—70–80 cm.
*Strength.*—Resistant to hot and cold weather.
*Branching character.*—Freely branching and lateral branching at every node.
*Number of branches per plant.*—7 branches/plant.
*Crop time to produce of a mature flowering plant.*—12 weeks.

The stem:
*Diameter.*—1–2 mm.
*Shape.*—Cylindrical.
*Anthocyan pigmentation.*—Present in older stems, between RHS 59A and N 79B.
*Length of internode.*—4–7 cm depending on light conditions.
*Pubescence.*—Absent.
*Color.*—Young stem: 146A. Older stem: 152A with some anthocyanin pigmentation.
*Stem length.*—30–35 cm.

The foliage:
*Arrangement.*—Opposite, but alternate on flower stems.
*Shape of leaf.*—2-pinnate fern-like leaves, entire leaves.
*Leaf apex.*—Apiculate.
*Leaf base.*—Acute.
*Texture.*—Smooth young leaves.
*Leaf length.*—2.5–3.5 cm.
*Leaf width.*—1.5–2.5 cm.
*Depth of incision.*—Fully incised.
*Color.*—Upper side: Young leaf 146B. Old leaf 137A. Lower side: Young leaf 147B. Old leaf 147B.
*Pubescence.*—Little hairy.
*Petiole.*—Length: 0.5–1.0 cm. Color: 146A.
*Venation.*—Shape: Pinnate. Color: 146B.

The bud:
*Puduncle length.*—6–10 cm.
*Peduncle color.*—RHS 152A.
*Size bud.*—Diameter: 0.3–0.5 cm. Length: 0.5–1.0 cm.
*Shape bud.*—Oblong.
*Color bud.*—14A.

Inflorescence:
*Diameter.*—3–3.5 cm.
*Form.*—Capitulum with 1 series of ray florets and more series of disc florets.
*Depth.*—3 mm.
*Overlapping of ray florets.*—Separate ray florets, but little overlap in flowerhead.
*Receptacle.*—Shape: Brush-shape. Height: 4 mm. Color: 147B.
*Involucre.*—8 bracts in 1 series. Color: 144A.
*Fragrance.*—Weak.
*Number of inflorescences per plant.*—±70 inflorescences per plant depending on growth conditions and age of plant.
*Lastingness of inflorescences.*—7 days.

Ray florets:
*No. of ray florets per inflor.*—5.
*Size.*—Length: 17–20 mm. Width: 11–13 mm.
*Shape of florets.*—Ovate with 2 light furrows.
*Color.*—More bright and intense golden yellow than 9A.
*Ray floret's apex.*—Rounded.
*Ray floret's base.*—Attenuate.
*Ray floret's margin.*—Entire.
*Ray floret's texture.*—Smooth.

Disc florets:
*No. of disc florets per inflor.*—±70 disc florets/inflorescence.
*Size.*—Length: 7 mm. Width: 1 mm.
*Shape of florets.*—Tubular.
*Color.*—13A.
*Disc area diameter.*—6–7 mm.

Androecium (on disc florets):
*Anther color.*—200A.
*Pollen color.*—17A.
*Amount of pollen.*—Few.

Gynoecium (on ray florets):
*Pistil number.*—±70 pistils/inflorescence.
*Style color.*—17B.
*Stigma color.*—17B.

Seed:
*Production.*—Yes.
*Seed length.*—0.5–0.7 cm.
*Seed diameter.*—0.1 cm.
*Color.*—202A.
*Shape.*—2 rigid awns with minute reflexed points on the achene.

Disease resistance and tolerance for weather conditions: Good tolerance to heat. The instant plant is an annual variety. It is not winterhard. Strong resistance to pests and diseases.

What is claimed is:

1. A new and distinct variety of *Bidins* plant, substantially as herein illustrated and described, characterized particularly as to novelty by its upright vigorous plant habit with bright golden yellow inflorescences.

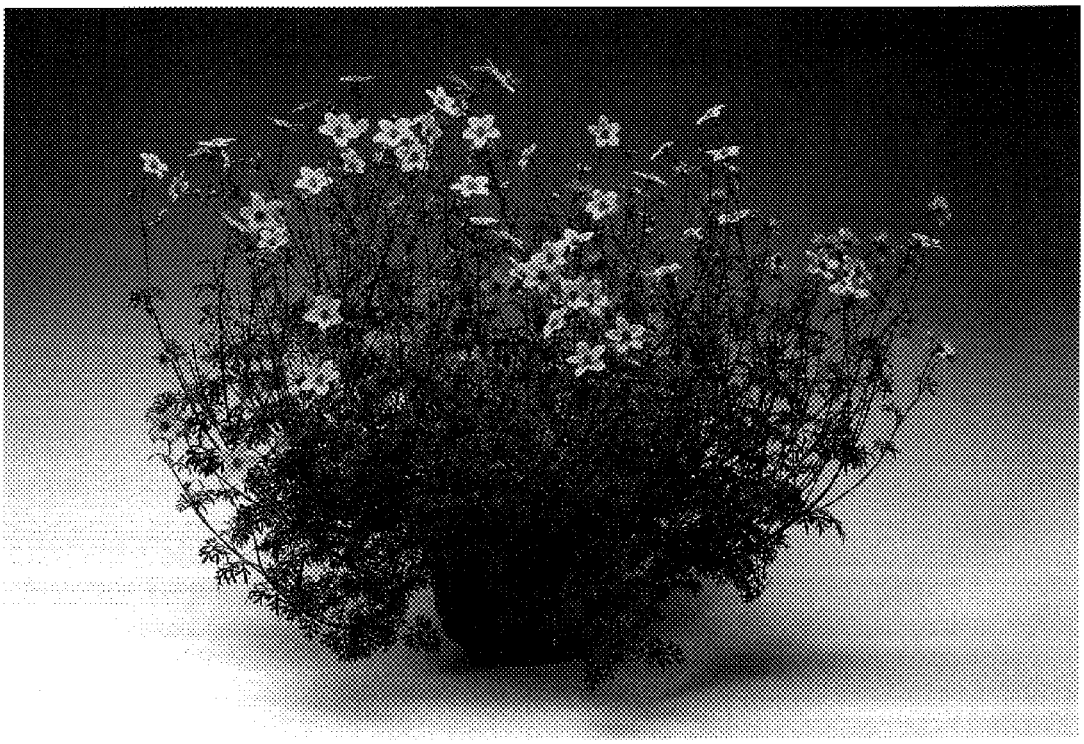

* * * * *